United States Patent [19]
Goldberg et al.

[11] Patent Number: 5,773,260
[45] Date of Patent: Jun. 30, 1998

[54] RIBOZYME COMPOSITIONS AND EXPRESSION VECTORS

[75] Inventors: Allan R. Goldberg; Shaji T. George; Hugh D. Robertson, all of New York, N.Y.

[73] Assignee: Innovir Laboratories, Inc., New York, N.Y.

[21] Appl. No.: 458,404

[22] Filed: Jun. 2, 1995

Related U.S. Application Data

[62] Division of Ser. No. 370,546, Jan. 9, 1995, which is a continuation of Ser. No. 212,310, Mar. 14, 1994, abandoned, which is a continuation of Ser. No. 66,897, May 21, 1993, abandoned, which is a division of Ser. No. 495,340, Mar. 19, 1990, Pat. No. 5,225,347, which is a continuation-in-part of Ser. No. 411,713, Sep. 25, 1989, Pat. No. 5,225,337.

[51] Int. Cl.$^6$ ............................. C12Q 1/68; C12P 19/34; C12N 15/00; C12N 15/64
[52] U.S. Cl. ......................... 435/91.31; 435/6; 435/69.1; 435/91.4; 435/172.1; 435/320.1; 536/23.1; 536/23.2; 536/24.5
[58] Field of Search ......................... 435/6, 91.31, 91.4, 435/69.1, 172.1, 320.1; 536/23.1, 23.2, 24.5

[56] References Cited

U.S. PATENT DOCUMENTS 4,987,071  1/1991  Cech et al. ........................... 435/91.31

FOREIGN PATENT DOCUMENTS

PCT/US87/03161  6/1988  WIPO .
PCT/US88/00478  6/1989  WIPO .

OTHER PUBLICATIONS

Crystal, "Transfer of Genes to Humans: Early Lessons and Obstacles to Success," Science 270:404–410 (1995).
Hsieh and Taylor, "Delta Virus as a Vector For the Delivery of Biologically–Active RNAs: Possibly A Ribozyme Specific for Chronic Hepatitis B Virus Infection" Innovations in Antiviral Development, Plenum Press, NY 1982.
Johnston, et al., "Present Status and Future Prospects for HIV Therapies," Science, 260:1286–1293 (May 1993).
Papas, Oncogenesis and AIDS (Greece, 1989).
Cech, Robert A. Welch Foundation Conferences on Chemical Research, pp. 345–350 (Nov. 4–6, 1985).
Reed, et al., Cell 30, 627–636 (1982).
Guerrier–Takada, et al., Cell 45, 177–183 (1986).
McClain, et al., Science 238, 527–528 (1987).
Altman, et al., Gene 82, 63–64 (1989).
Guerrier–Takada, et al., Science 246, 1578–1584 (1989).
Baer, et al., Nucleic Acids Research 18(1), 97–103 (1989 or 1990).
Lee, et al., Mol. Cell. Biol. 9(6), 2536–2543 (Jun. 1989).
Pace, et al., Gene 82, 65–75 (1989).
Pace, et al., J. Biol. Chem. 265(7), 3587–3590 (1990).
Altman, Advances in Enzymology A. Meister, ed., vol. 62, pp. 1–36, John Wiley & Sons, 1989.
Uhlenbeck, Nature 328, 596–600 (1987).
Kruger, et al., Cell 31, 147–157 (1982).
Zaug, et al., Nature 301, 578–583 (1983).
Zaug, et al., Science 224, 574–578 (1984).
Sullivan, et al., Cell 42, 639–648 (1985).
Been, et al., Cell 47, 207–216 (1986).
Inoue, et al., J. Mol. Biol. 189, 143–165 (1986).
Zaug, et al., Science 231, 470–475 (1986).
Surratt, et al., Molecular Biology of RNA 79–88 (Alan R. Liss, Inc., 1989).
Bonino, et al., J. Virology 58(3), 945–950 (Jun 1986).
Prody, et al., Science 231, 1577–1580 (Mar. 1986).
Wang, et al., Nature 323, 508–514 (Oct. 1986).
Kos; et al., Nature 323, 558–560 (Oct. 1986).
Chen, et al., Proc. Natl. Acad. Sci. USA 83, 8774–8778 (Nov. 1986).
Zaug, et al., Nature 324, 429–433 (Dec. 1986).
Joyce, et al., Proc. Natl. Acad. Sci. USA 84, 4398–4402 (Jul. 1987).
Darnell, Scientific American.
Taylor, et al., J. Virology 61(9), 2891–2895 (Sep. 1987).
Joyce and Inoue, Nucleic Acids Res. 15, 9825–9840 (1987).
Kay and Inoue, Nucleic Acids Res. 15, 1559–1577 (1987).
Pechan, et al., Z. Naturforsch. 42c, 1006–1008 (1987).
Kim and Cech, Proc. Natl. Acad. Sci. USA 84, 8788–8792 (Dec. 1987).
Hadid; Molecular Plant Pathology 78(5), 575–578 (1988).
Salazar, et al., J. gen. Virol. 69, 879–889 (1988).
Been' and Cech, Science 239, 112–1416 (Mar. 1988).
Abouhaidar and Paliwal, J. gen. Virol. 69, 2369–2373 (1988).
Kuo, et al., J. Virology 62:1855–1861 (Jun. 1988).
Negro, et al., J. Infectious Diseases 158(1), 151 (Jul. 1988).
Zaug, et al., Biochemistry 27, 8924–8931 (1988).
Haseloff & Gerlach, Nature 334, 585–591 (Aug. 1988).
Baltimore, Nature 335, 395–396 (Sep. 1988).

(List continued on next page.)

Primary Examiner—Nancy Degen
Assistant Examiner—Sean M. Garry
Attorney, Agent, or Firm—Arnall Golden & Gregory, LLP

[57] ABSTRACT

Hepatitis delta is used as a vector for inhibition of viral infection and to express proteins in vivo in a cell-specific manner. The scope of delta's use as a vector is broadened in the present invention in several important ways. For example, a delta RNA genome capable of self-replication is enlarged to carry additional information, either coding for messenger RNA for a protein, or for a targeted ribozyme, which can be delivered to liver cells using delta's normally infectious properties, or to other cell types using chimeric delta viral agents carrying altered surface proteins. In another embodiment, the delta vector is made self-limiting, so that its role in delivering targeted information is separated from its viral property of unlimited infectious replication. Targeting is achieved through the use of sequences flanking the delta sequences that have affinity for sites on RNA to be cleaved.

20 Claims, 3 Drawing Sheets

OTHER PUBLICATIONS

Cech, JAMA 260(20), 3030–3034 (Nov. 1988).
Sharp, JAMA 260(20), 3030–3034 (Nov. 25, 1988).
Taira, et al., *Nucleic Acids Research* 17(10); 3699–3708 (1989).
Wu and Lai, *Science* 243, 652–654 (Feb. 1989).
Ruden and Gilboa, J. Virol. 63(2), 677–682 (Feb. 1989).
Branch, et al., *Science* 243, 649–652 (3 Feb. 1989).
Wu, et al., *Proc.Natl. Acad. USA* 86, 1831–1835 (Mar. 1989).
Waugh, et al., *Science* 244, 1569–1571 (Jun. 1989).
Doudna and Szostak, *Nature* 339, 519–522 (Jun. 1989).
Cech, *Nature* 339, 507–508 (Jun. 1989).
Latham and Cech, *Science* 245, 276–282 Jul. 1989).
"Self–Cleaving RNA as an Anti–HIV Agent: Design and Delivery to Cells" (Developmental Therapeutics Branch AIDS Program, National Institute of Allergy and Infectious Diseases Jun. 21–23, 1989).
Maddox, *Nature* 342, 409–413 (Dec. 1989).
Young, et al., *Nature* 343, 28 (Jan. 1990).
Branch, Andrea D. and Hugh D. Robertson, "Efficient trans cleavage and a common structural motif for the ribozymes of the human hepatitis δ agent," *Proc. Natl. Acad. Sci USA* 88:10163–10167 (1991).
Branch, Andrea D., et al., "Ultrviolet light–induced crosslinking reveals a unique region of local tertiary structure in potato spindle tuber viroid and HeLa 5S RNA," *Proc. Natl. Acad. Sci. USA* 82:6590–6594 (185).
Branch, Andrea D., et al., "An Ultraviolet–Sensitive RNA Structural Element in a Viroid–Like Domain of the Hepatitis Delta Virus," *Science* 243:649–652 (1989).
Branch, Andrea D., et al., "The Novel Tertiary Structure in Delta RNA May Function as a Ribozyme Control Element," *The Hepatitis Delta Virus* 257–264 (1991).
Capel, Blanche, et al., "Circular Trnascripts of the Testis-–Determining Gene Sry in Adult Mouse Tests," *Cell* 73:1019–1030 (1993).
Casey, John L., et al., "A genotype of hepatitis D virus that occurs in northern South America," *Proc. Natl. Acad. Sci. USA* 90:9016–9020 (1993).
Green, Michael R., et al., "Biochemical Mechanisms of Constitutive and Regulated Pre–mRNA Splicing," *Ann. Rev. Cell. Biol.* 559–599 (1991).
Kumar, P.K.R., et al., "Random mutations to evaluate the role of bases at two important single–stranded regions of genomic HDV ribozyme," *Nucleic Acids Research* 20(15):3919–3924 (1992).

Lescure, Franck, et al., "Trans Cleavage of RNA Substrates by an HDV–Derived Ribozyme," *Hepatitis Delta Virus* 99–108 (1993).
Nishikawa, Satoshi, et al., "Identification of important bases for the self–cleavage activity of two single–stranded regions of genomic HDV ribozyme," *19th Symposium on Nucleic Acids Research* (Nov. 1992) (Japan).
Perrotta, Anne T. and Michael D. Been, "The self–cleaving domain from the genomic RNA of hepatitis delta virus: sequence requirements and the effects of denaturant," *Nucleic Acids Research* 18(23):6821–6827 (1990).
Perrotta, Anne T. and Michael D. Been, "A speudoknot–like structure required for efficient self–cleavages for hepatitis delta virus RNA," *Nature* 350:434–436 (1991).
Robertson, H.D., "Replication and Evolution of Viroid–Like Pathogens," *Current Topics in Microbiology and Immunology* 176 (1992).
Saldanha, Roland, et al., "Group I and group II Introns," *The FASEB Journal* 7:15–25 (1993).
Smith, Janet B. and Gail Dinter–Gottlieb, "Antigenomic Hepatitis delta virus ribozymes self–cleave in 18 M formamide," *Nucleic Acids Research* 19(6):1285–1289 (1990).
Smith, Janet B., et al., "A Sequence Element Necessary for Self–Cleavage of the Antigenomic Hepatitis Delta RNA in 20 M Formamide," *Biochemistry* 31:9629–9635 (1992).
Sogin, Mitchell L. and Jeffrey C. Edman, "A self–splicing intron in the small subunit rRNA gene of *Pneumocystis carinii*," *Nucleic Acids Research* 17(13):5349–5359 (1989).
Suh, Young–Ah, et al., "Deletion of Internal sequence on the HDV–ribozyme: elucidation of functionally important single–stranded loop regions," *Nucleic Acids Research* 20(4) 747–753 (1991).
Tanner, N. Kyle, "The Catalytic RNAs from Hepatitis Delta Virus: Structure, Function and Applications," *The Unique Hepatitis Delta Virus* 1–33 (1994).
Wu, Huey–Nan and Michael M. C. Lai, "RNA Conformational Requirements of Self–Cleavage of Hepatitis Delta Virus RNA," *Molecular and Cellular Biology* 10(10):5575–5579 (1990).
Wu, Huey–Nan and Zhi–Shun Huang, "Mutagenesis analysis of the self–cleavage domain of hepatitis delta virus antigenomic RNA," *Nucleic Acids Research* 20(22):5937–5941 (1992).
Wu, Huey–Nan, et al., "Mutagenesis analysis of a hepatitis delta virus genomic ribozyme," *Nucleic Acids Research* 21(18):4193–4199 (1993).

36 nm

Schematical structure of HDV fig. 3

```
                           c u
                          c   g
                          a   a      685/686
                          u   u    ←
                           ug                                    c u
662  G C G U u C C AuccuU U C   G C C G G CauGgucC C A G C    c
771  C G C A g G G U      A A G C G G C C G  C    G G U C G   c
                           U g                                  c u
                            g
                           C G
                           G C
                            a
                            a
                           G C
                           U A
                           A U
                           A U
                            u
                           G C
                           G C
                           C G
                           U A
                           C G
                           C G
                           C G
                           C G
                           u   a
                           g   c
                            c
```

RIBOZYME COMPOSITIONS AND EXPRESSION VECTORS

This is a divisional of copending application U.S. Ser. No. 08/370,546 filed Jan. 9, 1995, by Allan R. Goldberg, Shaji T. George, and Hugh D. Robertson, entitled "Therapeutic Ribozyme Compositions and Expression Vectors," which is a continuation of U.S. Ser. No. 08/212,310 filed Mar. 14, 1994, now abandoned, which is a continuation of U.S. Ser. No. 08/066,897 filed May 21, 1993, now abandoned, which is a divisional of U.S. Ser. No. 07/495,340 filed Mar. 19, 1990, now U.S. Pat. No. 5,225,347, which is a continuation-in-part of U.S. Ser. No. 07/411,713 filed Sep. 25, 1989, now U.S. Pat. No. 5,225,337.

BACKGROUND OF THE INVENTION

This invention is in the general area of genetic engineering of nucleic acid sequences, especially RNA sequences having protein encoding or ribozyme activity derived from hepatitis delta virus.

Constructing vectors for delivery of therapeutic ribozymes and/or mRNA sequences to target cells is a difficult challenge. In U.S. Pat. No. 5,225,337, vectors created from retroviruses were described as a means for delivering therapeutic ribozymes capable of cleaving viral mRNAs to limit viral infections. In one embodiment, the ribozyme from the RNA of the hepatitis delta virus in combination with appropriate T-cell specific retroviruses was described as a means of targeting and cleaving RNAs in cells infected with human immunodeficiency virus (HIV). U.S. Pat. No. 5,225,337 also outlined a method to use the delta viral RNA genome as a vector, carrying information from one cell to another.

Historical Background. Discoveries in the basic realm of molecular biology over the past five years have led to the realization that RNA has a series of distinct capabilities and biological activities previously unsuspected. The most important of these novel RNA-level discoveries has been the finding that RNA can be an enzyme as well as an information carrier.

Since 1982, several unexpected diseases caused by RNA-based pathogenic agents have emerged. These include the lethal Acquired Immune Deficiency Syndrome (AIDS) and delta hepatitis, a particularly virulent form of fulminant hepatitis caused by a viroid-like RNA agent. These blood-borne diseases are spread at the RNA level, manifest themselves in cells of patients, and are by now present within the bloodstream of millions of individuals. Conventional biotechnology, with its reliance on recombinant DNA methods and DNA-level intervention schemes, has been slow to provide valid approaches to combat these diseases.
Hepatitis B Virus (HBV).

HBV, a member of a group of small DNA-containing viruses that cause persistent noncytopathic infections of the liver, is an infectious agent of humans that is found worldwide and which is perpetuated among humans in a large reservoir of chronic carriers. It is estimated that about 6–7% of the earth's population is infected (300 million carriers). The prevalence of the infection is not uniform throughout the world. There is a geographic gradient in distribution of HBV. It is lowest in North America and Western Europe, where the virus can be detected in 0.1 to 0.5% of the population, and highest in Southeast Asia and sub-Saharan Africa, where the frequency of infection may vary from 5 to 2.0 of the population. This skewed distribution parallels that of hepatocellular carcinoma and provides strong epidemiologic evidence for an association between chronic HBV infection and this type of malignancy.

Hepatitis B is of great medical importance because it is probably the most common cause of chronic liver disease, including hepatocellular carcinoma in humans. Infected hepatocytes continually secrete viral particles that accumulate to high levels in the blood. These particles are of two types: (i) noninfectious particles consisting of excess viral coat protein (HBsAg) and containing no nucleic acid (in concentrations of $10^{13}$ particles/ml blood), and (ii) infectious, DNA-containing particles (Dane particles) consisting of a 27 nm nucleocapsid core (HBcAg) around which is assembled an envelope containing the major viral coat protein, carbohydrate, and lipid, present in lower concentrations ($10^{10}$ particles/ml blood). The DNA genome is about 3000 nucleotides in length, circular and partially single-stranded, containing an incomplete plus strand. The incomplete plus strand is complexed with a DNA polymerase in the virion which, under appropriate in vitro conditions, can elongate the plus strand using the complete minus strand as the template. These morphological and structural features distinguish hepatitis B viruses from all known classes of DNA-containing viruses.

The replication cycle of hepatitis B viruses is also strikingly different from other DNA-containing viruses and suggests a close relationship with the RNA-containing retroviruses. The principal unusual feature is the use of an RNA copy of the genome as an intermediate in the replication of the DNA genome. Infecting DNA genomes are converted to a double-stranded form(s) which serve(s) as a template for transcription of RNA. Multiple RNA transcripts are synthesized from each infecting genome, which either have messenger function or DNA replicative function. The latter, termed "pre-genomes," are precursors of the progeny DNA genomes because they are assembled into nucleocapsid cores and reverse-transcribed into DNA before coating and export from the cell. Thus each mature virion contains a DNA copy of the RNA pre-genome and a DNA polymerase.

The first DNA to be synthesized is of minus strand polarity and is initiated at a unique site on the viral genetic map. Very small nascent DNA minus strands (less than 30 nucleotides) are covalently linked to a protein, and are likely to act as primer for minus strand DNA synthesis. Growth of the minus strand DNA is accompanied by a coordinate degradation of the pre-genome so that the product is a full-length single-stranded DNA, rather than an RNA:DNA hybrid. Plus strand DNA synthesis has been observed only after completion of the minus strand, and initiates at a unique site close to the 5' end of the minus strand. Complete elongation of the plus strand is not a requirement for coating and export of the nucleocapsid cores, thus most extracellular virions contain incomplete plus strands and a large single-stranded gap in their genomes.

The Causative Agent of Delta Hepatitis: Hepatitis Delta Virus (HDV)

The first evidence for the existence of hepatitis delta agent was the discovery by Dr. Mario Rizzetto in 1977 in Italy of the delta hepatitis antigen as a novel nuclear antigen in liver biopsies from patients with chronic hepatitis B virus. Carriers expressing this antigen exhibited a greater incidence of severe chronic active hepatitis and cirrhosis; the antigen was also implicated in a substantial number of cases of fulminant hepatitis. Chimpanzee transmission studies showed that a defective viral agent was associated with delta hepatitis, and that, to replicate, this agent required HBV or another hepadna virus. It was later shown that HDV replicates efficiently and suppresses helper replication, and can thereby lead to substantially higher titers of HDV relative to the hepadna virus.

HDV is now known to be endemic among the HBV carrier population in all parts of the world, where it occurs either as the result of super-infection of the HBV carrier individuals or as an acute co-infection. The consequences of the infection seem to depend upon the prior status of the patient with respect to HBV. Co-infection with both HBV and HDV of an HBV-naive individual is apparently less dangerous than the superinfection of an individual who already has a chronic active HBV infection. In the latter case, the apparent extent of liver damage is greatly enhanced with a major risk of death from fulminant hepatitis. Examples of the latter are epidemics of HDV in parts of South America and Central Africa. The virus is found in southern Europe, the Middle East, and parts of Africa, South America, and the South Pacific. Interestingly, HDV infection is somewhat rare in the Orient even though the prevalence of HBV is high in that part of the world. The spread of HDV is by mechanisms similar to that of HBV, by parenteral and transmucosal routes, so the population at risk in non-endemic areas is similar. These include, in order of frequency, intravenous drug addicts, recipients of blood products, and male homosexuals.

In infectious sera, HDV particles of about 35–37 nm in diameter have been distinguished from the 42 nm Dane particles and 22 nm surface antigen moieties derived from HBV. The HDV virions have an envelope in which the hepatitis B surface antigen (HBsAg) is embedded. This complex encapsidates the hepatitis delta antigen (HDAg) and the single-stranded RNA genome of 1.7 kilobases (kb) (FIG. 1).

Molecular studies of the HDV RNA genome have shown that it has a circular conformation, unlike any other known animal virus, and has the ability to fold on itself by intramolecular base pairing to form an unbranched rod structure. The generation of recombinant probes to HDV has made it possible to study the intracellular replication of the genome. HDV replication is unlike that of the helper hepadnavirus in that it does not involve reverse transcription. HDV genome replication actually involves the copying of the genomic RNA into a complementary RNA, called the antigenomic RNA, which in turn acts as the template for the synthesis of more genomic RNA. In infected cells the genomic RNA is present in approximately 5- to 20-fold excess relative to the antigenomic RNA. HDV genomic RNA can accumulate in the infected liver to a level of 1% of all liver RNA, which corresponds to an average of 300,000 copies per liver cell.

In summary, several aspects of HDV genome replication serve to differentiate this virus from other animal viruses: the HDV virion genome is a single-stranded RNA of about 1,700 nucleotides; at least 96% of the genomic RNA is in a circular conformation; the genomic RNA has the ability to fold on itself by base pairing to create an unbranched structure; intracellularly, there is not only genomic RNA but also, in a relatively lower amount, a complementary RNA called the antigenomic RNA; most of the intracellular genomic and antigenomic RNA species are monomeric, of unit genome length; most of those monomers have a circular conformation; multimeric lengths of genomic and antigenomic RNAs are present intracellularly at low levels relative to monomeric RNA.

Current evidence indicates that the rolling-circle model of replication for plant viroids is applicable to HDV, as reported by Chen, et al., *Proc. Natl. Acad. Sci. USA* 83: 8774–8778 (1986). This mode of replication requires RNA cleavage and ligation to produce progeny monomer circles, reactions which can occur in vitro with HDV RNA in the absence of proteins. Several laboratories have demonstrated that ribozyme activities, sequence-specific RNA catalysts, are embodied within the genomic and anti-genomic sense strands of HDV. Self-cleavage has been shown to occur at unique sites on each strand and the junction fragments, as in virusoid self-cleavage, contain a cyclic 2'3'-monophosphate and 5'-hydroxyl termini. In addition, it has been shown that subfragments, of 110 nucleotides or less around the cleavage site, of delta RNA can undergo autocatalytic cleavage at a faster rate and relatively low $Mg^{2+}$ concentrations, in comparison with other ribozymes.

Background on ribozymes:

There are five classes of ribozymes now known which are involved in the cleavage and/or ligation of RNA chains. A ribozyme is defined as an enzyme which is made of RNA, most of which work on RNA substrates. Ribozymes have been known since 1982, when Cech and colleagues (*Cell*, 31: 147–157) showed that a ribosomal RNA precursor in tetrahymena, a unicellular eukaryote, undergoes cleavage catalyzed by elements in the RNA sequence to be removed during the conversion of the rRNA precursor into mature rRNA. This sequence to be removed (called an intervening sequence or intron) is one of what are now known to be numerous examples of "Class I" intron ribozyme activities. A similar "Class II" intron ribozyme mechanism was discovered more recently, involving the cleavage and subsequent ligation of a number of yeast mitochondrial RNAs (*Nature*, 324: 429–433). Cech and colleagues described certain in vitro applications of "class I" ribozymes in PCT/US887/03161 by University Patents, Inc., (published as WO 88/04300 16 Jun. 1988). Their potential for therapeutic applications in cells and in patients remains unclear.

A third class of ribozyme, discovered in 1983, was the first to be shown to work in trans (i.e., to work under conditions where the ribozyme is built into one RNA chain while the substrate to be cleaved is a second, separate RNA chain). This ribozyme, called M1 RNA, was characterized in 1983 by Altman and colleagues as responsible for the cleavage which forms mature 5' ends of all transfer RNAs (tRNAs) in *E. coli*. Analogous RNA ribozymes concerned with tRNA synthesis have since been found in all cells in which they have been sought, including a number of human cell lines.

The two remaining ribozyme classes are related to the replication cycle of a group of self-replicating RNAs called "viroid-like pathogens", or VLPs. Plant viroids, RNA satellites of plant viruses, and the delta agent are all members of the VLP group. In 1984, Branch and Robertson (*Science*, 233: 450–455) published the replication cycle strategies for these pathogens, subsequently verified by experiments conducted in several laboratories. A key element of this "rolling-circle" replication strategy is that the VLP undergoing replication makes greater-than-unit-length copies of its information, which are then cleaved to monomeric size by ribozyme activities built into the RNA of the VLP itself. One class of VLP ribozymes is defined by a small structural domain, consisting of only about 30 nucleotides, called a "hammerhead". Uhlenbeck (*Nature* 328, 596–600, 1987) and Forster and Symons (*Cell* 50, 9–16, 1987), defined the requirements for cleavage by this ribozyme class. Various embodiments and potential applications have also been described by Haseloff, Gerlach and Jennings in PCT/AU88/00478 by Commonwealth Scientific and Industrial Research Organization (published as WO 90/05852 29 Jun. 1989).

The delta agent RNA also replicates by a rolling circle mechanism, and ribozymes are key in cleaving multimeric genomic and anti-genomic RNAs to monomers. Sharmeen at. al., *J. Virol.*, 62, 2674–2679 (1988); Branch, et. al.,

*Science*, 243, 649–652 (1989); and Wu and Lai, *Science* 243, 652–655 (1989), defined the ribozyme cleavage points of both delta strands and the domains containing them. In U.S. Ser. No. 07/411,713, the properties of these ribozyme elements were summarized and their use in anti-viral therapy delineated.

It is an object of the present invention to provide methods and compositions for delivering therapeutic entities incorporating targeted ribozymes to cells to bring about a specific therapeutic effect therein.

It is another object of the present invention to provide methods and compositions for delivering genes encoding specific proteins to cells, such as hepatocytes, for expression therein.

It is a further object of the invention to provide methods and compositions based on hepatitis delta virus, or other viruses, whose replication cycle is or can be engineered to be self-limiting.

SUMMARY OF THE INVENTION

The scope of delta's use as a vector is broadened in the present invention in several important ways. In one embodiment, a delta RNA genome capable of self-replication is enlarged to carry additional information, either coding for messenger RNA for a protein, or for a targeted ribozyme, which can be delivered specifically to liver cells using delta's normally infectious properties, or to other cell types using chimeric delta viral agents carrying altered surface proteins. In another embodiment, the delta vector is made self-limiting, so that its role in delivering targeted information is separated from its viral property of unlimited infectious replication. Targeting of RNA is achieved through the use of sequences in the vicinity of the delta sequences which interact specifically with sequences at or near the site to be cleaved.

These embodiments are particularly useful in the treatment of viral diseases such as hepatitis B and human immunodeficiency virus (HIV) infections.

BRIEF DESCRIPTION OF THE DRAWINGS

FIG. 3 is the proposed secondary structure of the 110 (662–771) nucleotide subfragment of the genomic sequence of hepatitis delta which possesses autocleavage activity. Arrow indicates the site of cleavage. The top half of the stem (nucleotides 662–707) depicts the putative substrate half of the self-cleaving RNA while the bottom half of the stem (nucleotides 708–771) depicts the putative enzyme half of the molecule. This example of a proposed secondary structure was derived using Tinoco energy rules and the dynamic programming rules of Zuker.

DETAILED DESCRIPTION OF THE INVENTION

Figure 1:
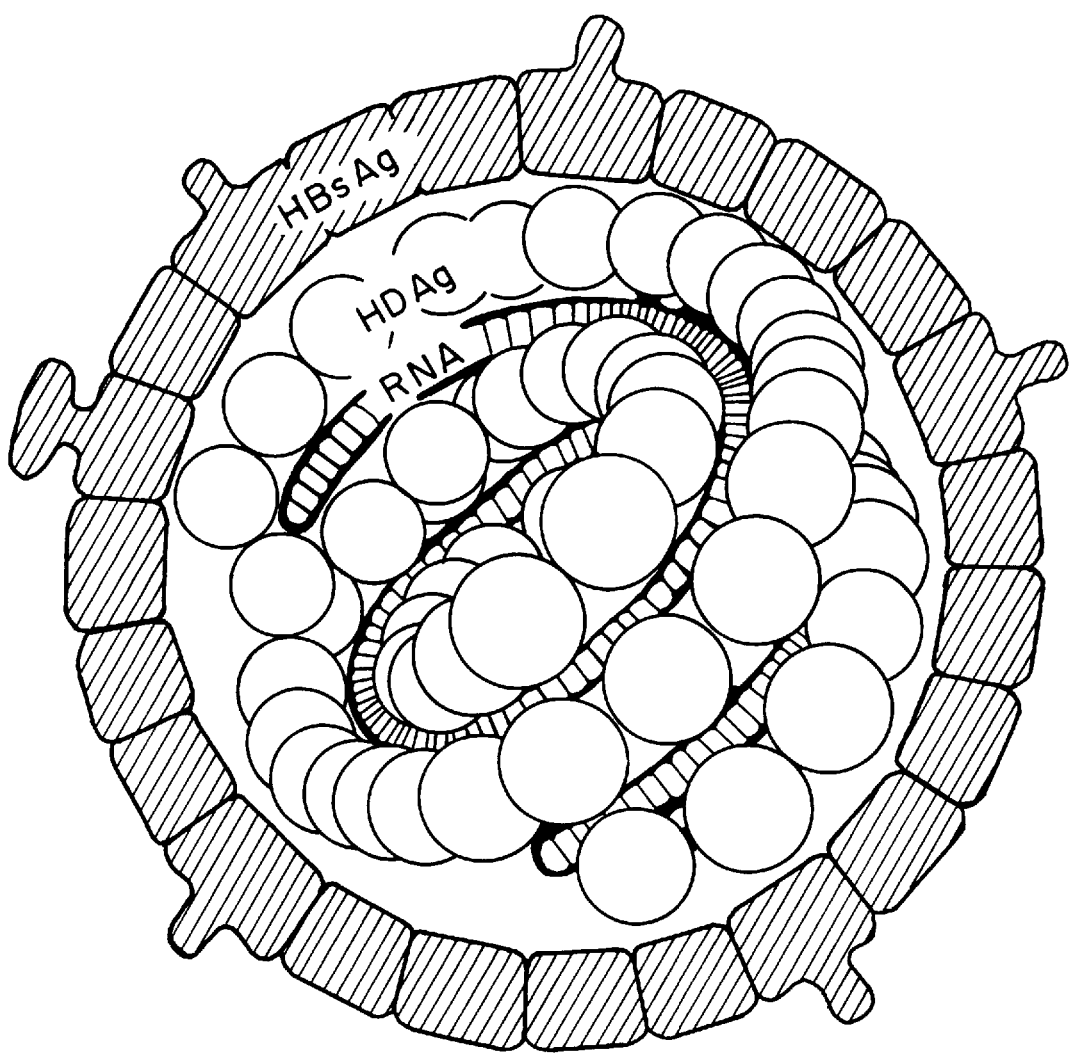
FIG. 1 is a schematic of the structure of HDV. The envelope (shaded) composed of HBsAg is derived from hepadna viruses (hepatitis B). The interior contains a self-annealing circular RNA and the delta antigen (HDAg).

While ribozymes are an important part of the delta viral RNA life cycle, and represent one of the several therapeutic approaches using delta RNA vectors described herein, the major underlying theme of the methods and vectors disclosed here is that delta RNA can be used as a self-limiting vector to carry therapeutic information (in the form of ribozyme RNAs or proteins) into liver and other cells; and that delta vectors can do all of this at the RNA level without involving or altering the chromosomal DNA in the cells of the treated patient.

Delta viral RNA vectors have been constructed carrying the ribozymes needed for their own amplification as well as those targeted for specific RNA sequences in pathogenic agents. The principal emphasis here is on the role of delta virus as a vector to deliver mRNA sequences and ribozymes to appropriate targets, and to use the self-replicating capability of delta to amplify the needed information for the most effective therapy. Information can be added to the basic genome comprising at least 1100 bases above the canonical 1679-base length, so that targeted ribozymes or templates for mRNA can be carried into target cells, where their RNA will be amplified, and/or work in trans on specific target RNA sequences. In the latter case, targeting sequences are added to the delta genome and the composite RNAs packaged into particles and introduced into liver or other cells as appropriate. An enlarged delta genomic RNA is constructed embodying one or more additional ribozymes, over and above the two ribozymes required for the normal delta replication cycle described in the background of this invention. The additional ribozyme(s) is positioned at a point in the genome which does not interrupt any critical RNA structures, and will cleave in trans only when the targeted sequence of the virus being treated is detected.

The applications described in detail in the examples below can be summarized as follows: (1) Delivery to the liver of delta viral RNA embodying ribozyme activities targeted to HBV mRNAs; (2) Delivery to the liver of delta viral RNA carrying mRNA for specific liver or other non-liver proteins; (3) Construction of packaging cell lines for production of delta viral particles for delivery to the liver or other tissues; (4) Implementation of a built-in "self-limiting" approach to the delta-based RNA vectors to be used, allowing amplification of their information as RNA but limiting their spread as infectious agents; (5) Construction of "chimeric" delta vectors carrying altered surface proteins allowing them to target to non-liver cells, e.g. T-cells; and (6) Construction of defective, non-replication-competent retroviral vectors, as an alternative to delta vectors, missing part of the envelope (env) gene and/or other gene segments, for use as self-limiting alternative carriers of ribozymes.

These new vectors provide a therapeutic means to treat a variety of diseases, especially those of viral origin, as well as diseases resulting from a deficiency or defect in specific protein expression. For example, the pattern of growth and replication of hepatitis B, the helper virus providing surface protein for the delta viral particles, in liver cells capable of infection by delta vectors makes it particularly susceptible as a target for anti-viral therapy using the modified delta hepatitis vectors. Another virus particularly well suited for use as a target is the human immunodeficiency virus (HIV), using the modified delta vector to cleave and thereby inactivate critical RNA encoding HIV proteins and the HIV genome itself. A variety of disorders can be treated using the delta vectors to specifically infect and deliver RNA encoding the desired proteins to liver. For example, the genes encoding liver proteins such as coagulation factors or non-liver proteins such as insulin, can be directed to liver cells using the modified delta vectors.

There is a variety of available HDV sequences isolated from different geographic locations which show a spectrum of pathogenicity ranging from severe to very mild. For example, there is a strain isolated from the Mediterranean area (Naples) which presents with nearly 50% of patients having fulminant hepatitis (Sherlock, S. and Thomas, H. C. J. *Hepatology*, 3: 419–423 (1986)) in contrast with strains from the Pacific area (Melbourne) which showed no fulminant hepatitis in 100% of the cases (Jacobson, I. M., et al., J. *Hepatology*, 5: 188–191 (1985)). Use of the mild strains ensures virus vectors that are minimally toxic to the host.

The present invention will be further understood by reference to the following non-limiting examples.

EXAMPLE 1

Delivery to the liver of delta viral RNAs carrying ribozye activities targeted to HBV nRNAs.

Figure 2:
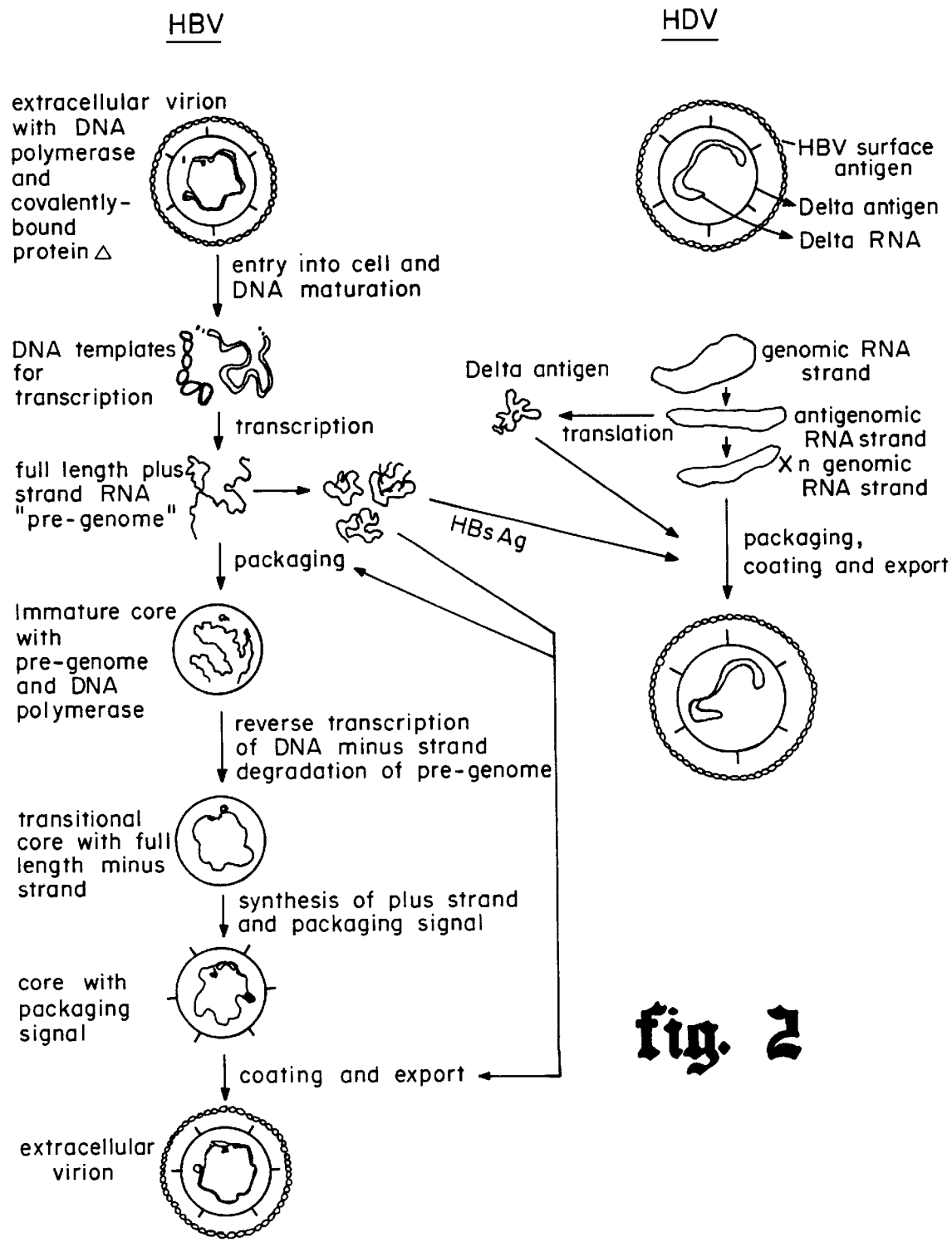
FIG. 2 is a schematic of infection and replication by HBV and coinfection and replication by HDV.

Hepatitis B virus (HBV) infection is common throughout the world, often causing severe disease symptoms and sometimes even death. As shown in FIG. 1, the envelopes of HDV virions have the hepatitis B surface antigen (HBsAg) on their exterior, which targets the viral particle to hepatic cells. The interior contains a self-annealing circular RNA and the delta antigen (HDAg). FIG. 2 is a schematic of infection and replication by HBV and coinfection and replication by HDV. The specific targeting ability of delta virus can therefore be used for the delivery of ribozyme activity directed against HBsAg mRNA, or against mRNA encoding other HBV proteins, to hepatic cells infected with HBV.

As described in U.S. Pat. No. 5,225,327 HDV RNA possesses an autocleaving ribozyme activity at position 685/686 on the genomic strand and at position 900/901 on the antigenomic strand, both of which are necessary for HDV replication. A 110 base fragment of the genomic RNA is capable of autocleavage. Analysis of the probable structure of this sequence, verifiable by ultraviolet cross-linking studies, reveals a closed structure with a spatial arrangement containing both a substrate and an enzyme portion, as shown in FIG. 3, and a cleavage site between nucleotides 685 and 686. Parts of this structure can be deleted without any effect on the ribozyme activity. Separation of the two halves confers one half (662–707) with substrate-like properties and the other half (708–771) with enzyme-like properties.

In one form of the construct having ribozyme activity directed against specific HBV RNA sequences, the stem portion of the enzyme half is replaced, for example, with a 15 nucleotide-long guide sequence complementary to the HBV RNA. The site is so chosen such that limited sequence similarity to the loop in the substrate half is maintained, especially around the cleavage site. Other forms of the construct having ribozyme activity would target cleavage sites by local tertiary RNA:RNA interactions or by common protein recognition of features on the enzyme and substrate RNAS. Such constructs are then capable of cleaving the HBV RNA at a site that is specified by the appropriate structural interactions.

Additional engineered ribozyme sequences can be built into HDV RNA at more than one site provided that they do not interfere with HDV replication. The cloning procedures are carried out on the cDNA sequence corresponding to the entire HDV genome, using standard polymerase chain reaction techniques to clone the anti-HBV ribozyme fragment into the HDV cDNA at the specified site. In one approach to constructing appropriate delta vectors, a sequential trimer of HDV cDNA is constructed and cloned into a eukaryotic SV40 expression vector plasmid downstream of a SV40 early gene promoter. The plasmid is then transfected into a hepatic cell line. The resulting RNA transcript is a trimeric RNA of the delta which is processed into self-replicating monomeric delta RNA. The SV40 promoter is necessary to produce the initial round of the trimeric RNA transcripts, which then becomes self-replicating. In a second approach to constructing appropriate delta vectors, appropriately engineered DNA inserts carrying delta sequences under the control of T7 or SP6 promoters can be transcribed in vitro with bacteriophage T7 or SP6 RNA polymerases and the resulting RNAs can be introduced into cell lines by lipofection or similar means.

This delta RNA is packaged in virions possessing HBsAg using special cell lines expressing HBsAg. Upon introduction of the engineered delta virus into the bloodstream of a patient infected with HBV, the delta virus specifically infects the hepatic cells. Once inside such cells, the delta virus replicates to produce high copy levels of the genome which can then cleave the HBsAg mRNA, other HBV mRNA, or the HBV pregenome RNA as specified by the ribozyme activity and thereby render the HBV genomes inactive.

Hepatitis delta virus possesses considerable internal complementarity in the sequence of its genome. By virtue of this property, the ribozyme region of the anti-genomic strand of delta is very similar in sequence to the ribozyme region of the genomic strand; however, the cleavage on the antigenomic strand occurs between nucleotides 900 and 901 instead of 685 and 686. Secondary structure predictions of the antigenomic strand around the ribozyme cleavage site reveal a very similar structure to that of the genomic strand shown in FIG. 3 with corresponding stems and loops. This structure can be engineered to produce both enzyme and substrate halves, as is the case for the genomic strand, that can function as a trans-acting ribozyme. Delta vectors also can be engineered to use this anti-genomic ribozyme activity to cleave HBV or other RNA molecules, as well as the ribozyme activity embodied within the genomic strand.

EXAMPLE 2

Example of using delta agent as an RNA-level vector for the specific delivery of protein-coding sequences.

As described above, delta virus has a specific tropism for liver because of the presence of HBsAg as the sole component of the virus coat, presumably by interaction with a specific and unique receptor on the liver cells for that antigen. Accordingly, a gene encoding a protein (to be preferentially expressed in hepatic cells) can be inserted with an appropriate start and stop codon for intracellular expression of that protein. The antigenomic strand of the delta has several open reading frames (ORFs) but only ORF5, which codes for the delta antigen, is translated in infected liver cells. Accordingly, the sequence coding for the protein of interest will be inserted under the control of these translational signals for construction of an expression vector targeting hepatic cells.

The isolation of a delta variant whose genome contains 2,942 nucleotides, in contrast with 1,679 nucleotides found in the canonical delta virus, demonstrates the feasibility of inserting extra protein coding sequences into the delta viral RNA.

In preferred applications in vivo, patients having deficiencies in liver proteins such as alcohol dehydrogenase or blood clotting proteins, such as anti-hemophilic factor, are infected with an appropriate delta viral RNA vector to enhance or replace the deficient or missing protein. Delta vectors carrying sequences for non-liver proteins, such as insulin, can also be infected into liver cells for systemic release.

EXAMPLE 3

Development of packaging cell lines for growth of delta viral particles for targeting of the liver or other tissues as appropriate.

Engineered delta viral RNAs, whether possessing ribozyme activities directed against viral or cellular mRNA, as described in Example 1 and modifications thereof, or possessing translatable RNA sequences for production of proteins, as described in Example 2, must be packaged into virions before they can be used as drug delivery vehicles for targeting information to specific tissues. In order to package delta RNA into virions coated with HBsAg, a trimer of the engineered delta cDNA under the control of a SV40 promoter is constructed and transfected into hepatic or other cell lines expressing large amounts of HBsAg. Such cell lines can be of mammalian (for example, HepG2) or yeast origin and can be easily constructed by transfection of the HBsAg gene under the control of an SV40 promoter, vaccinia virus promoter, or other appropriate promoter. Shuttle vector plasmids carrying the SV40 promoter are commercially available from Pharmacia.

Clones expressing large amounts of HBsAg are selected and grown in culture. When the engineered trimeric delta cDNA, or an appropriate RNA copy, is transfected or lipofected into these cell lines, the replicating delta packages itself in virions, to yield an RNA:delta-antigen complex enveloped by HBsAg protein. These virions bud from the membrane of infected cells and can be collected from the cell culture supernatant and used for subsequent infections. When the engineered ribozyme activity of the delta is directed against the HBsAg mRNA, a cell line that produces HBsAg RNA in excess of the capacity of the ribozyme to destroy it is used for production of the modified virus.

For the production of chimeric delta vectors, described in example 5, cell lines producing the specific surface antigen of the new delta virus vector must be used. For example, to package chimeric delta virus RNA into pseudo-HIV virions, the altered delta viral cDNA is transfected into a cell line expressing the HIV envelope glycoproteins. The resulting chimeric delta virions are surrounded by the HIV coat proteins and are able to specifically target $CD4^+$ cells in the same manner as wild-type HIV-1.

EXAMPLE 4

Development of "self-limiting" delta-based RNA vectors for amplification of their information as RNA but limited with respect to their spread as infectious agents.

The success of an anti-viral drug is measured by its ability both to destroy the pathogenic virus and to be minimally toxic to the host. To that end, virus vectors whose propagation is self-limiting have been created. This achievement is made possible in the case of delta virus because its replication is helper virus dependent (FIG. 2). Although delta virus RNA can replicate in any cell type, it cannot form infectious particles without the help of the HBV-supplied surface antigen, which is why infectious delta virus particles can only be produced in HBV-infected patients. Engineered delta virus vectors carrying a ribozyme directed against HBV surface antigen and/or core antigen mRNA or the HBV pregenome RNA, as detailed in Example 2, can be used to infect the liver of a HBV-infected patient, and thereby destroy the HBV by virtue of its anti-HBV ribozyme activity. By this process, the HDV deprives itself of the HBsAg necessary for further production of infectious delta particles. Eventually, when all the HBV RNA has been destroyed, the delta virus will no longer be able to produce infectious particles and its spread will thereby be limited. This self-limiting replication scheme also limits the toxic effects normally associated with viremia.

EXAMPLE 5

Development of chimeric delta vectors carrying altered surface proteins which allow them to be delivered to non-liver cells.

Although delta virus is an excellent vector for the specific delivery of ribozymes and mRNA sequences to liver cells by virtue of HBsAg on the surface of the virion, it cannot be used in unmodified form for the delivery of therapeutics to any other cell types. To circumvent this limitation, delta vectors with altered specificity for cell types other than hepatic cells are constructed.

Delta virus RNA encodes the delta antigen (HDAg), a 27 kd protein, on its anti-genomic strand. Genomic delta RNA is surrounded by this antigen before being enveloped by the HBsAg to form infectious HDV particles (FIG. 1). The amino terminal domain of the delta antigen binds strongly to the delta RNA. It is the C-terminal domain of the antigen that binds to HBsAg envelope protein provided by helper HBV.

Like delta virus, retroviral RNAs, such as HIV, are surrounded by a protein before they are directed into the budding envelope. The gag protein is the retroviral equivalent of the delta antigen. When delta RNA corresponding to the C-terminus of the delta antigen is replaced with RNA sequences encoding the gag protein of HIV, the product is a chimeric delta antigen-gag protein, which can bind to delta RNA by virtue of the delta antigen N-terminal sequences. When this delta RNA is replicated, as in example 3, in a cell line expressing the HIV envelope proteins, the RNA surrounded by the chimeric protein will package itself into virions whose envelope is composed of HIV proteins. These chimeric delta viral particles, by virtue of the HIV glycoprotein envelope, will have specificity for $CD4^+$ cells. If the genome of this delta virus is also carrying a ribozyme against the env or gag mRNA of HIV, as described in Example 1, and is used to superinfect T-cells previously infected with HIV, the chimeric delta virus will recognize the CD4 molecules on the T-cells and will infect those cells. The delta RNA will replicate and its HIV-specific ribozyme will destroy the HIV sequences. The delta vector will form new infectious particles as long as sufficient HIV env protein remains available to allow assembly and spread. Similarly, the chimeric vector can infect stem cell in vitro, which can then be used in an autologous bone marrow transplant in a partially cytoablated patient to create a population of T-cells that are resistant to HIV because of the presence of a ribozyme directed against HIV sequence(s).

The same technique can be used to create a variety of chimeric delta antigens possessing the N-terminus of the delta antigen and the surface antigen of another virus of choice to produce pseudo-virions with altered cell specificity.

EXAMPLE 6

Development of defective retroviral vectors for targeting ribozymes.

Retroviral vectors also can be used to target anti-viral ribozymes to various cell types. Unfortunately, only very limited numbers of human retroviruses are known which show specificity for limited number of cell types. In this example, defective viruses are used as a vector for ribozymes. The specific example uses a defective HIV vector carrying a ribozyme targeted to HIV mRNA. The vector can target itself to CD4+ cells but cannot produce infectious virions.

In one embodiment, a retroviral vector capable of targeting HIV infected cells is created by deleting 100–200 nucleotides from the env gene and replacing it with a ribozyme targeted against the same region of the HIV RNA or to other regions of the HIV RNA (for example gag). The engineered HIV RNA is packaged in cell lines expressing the surface glycoproteins of HIV. The resulting virus particles are isolated from the culture supernatant and used to infect patients infected with HIV. The defective HIV virus particles carrying the ribozyme are able to target to the CD4+ cells, where they are endocytosed and uncoated. These particles can then replicate and express the anti-HIV ribozymes and inactivate the HIV RNA particles. These altered HIV particles can form infectious particles only if they are provided with the envelope glycoproteins necessary for the formation of whole virions.

This general method can be applied to other retroviruses and possibly other non-retroviruses to produce defective and "self-limiting" viruses to carry ribozymes to destroy the native virus.

Modifications and variations of the methods and resulting targeted vectors having ribozyme activity will be obvious to those skilled in the art from the foregoing detailed description. Such modifications and variations are intended to come within the scope of the appended claims.

We claim:

1. A method for constructing a vector for delivering a ribozyme to a cell to specifically cleave RNA in the cell comprising:

providing cDNA transcribed as hepatitis delta virus RNA having ribozyme activity in combination with nucleotide sequences specifically binding targeted nucleotide sequences in the cell, wherein the hepatitis delta virus RNA contains sufficient sequence and is of appropriate secondary structure to replicate in the cell, and the targeted sequences position the ribozyme activity at a site to be cleaved.

2. The method of claim 1 wherein the hepatitis delta virus RNA comprises nucleotides between delta 708–771, further comprising altering the nucleotide sequence to maximize enzymatic activity.

3. The method of claim 2 wherein the stem portion of the enzymatically active delta virus RNA is substituted with binding sequences.

4. The method of claim 1 wherein the targeting sequences are synthesized based on a sequence of the viral genome to be cleaved.

5. The method of claim 4 wherein the viral genome is hepatitis B virus.

6. The method of claim 4 wherein a hepatitis delta virus-complementary viral sequence is cloned by the polymerase chain reaction.

7. The method of claim 1, wherein a sequential trimer of the hepatitis delta sequence is constructed.

8. The method of claim 7 wherein the trimer is cloned into a eukaryotic viral expression vector downstream of a viral early gene promoter.

9. The method of claim 8 wherein the vector and promoter virus is SV40.

10. The method of claim 1 wherein a greater than unit length DNA insert encoding the hepatitis delta sequence is constructed.

11. The method of claim 10 further comprising packaging the hepatitis delta virus construct into a cell line expressing a specific surface antigen recognized by selected cells.

12. The method of claim 11 wherein the construct is transfected into the cells.

13. The method of claim 11 wherein the greater than unit length delta RNA synthesized in vitro is lipofected into a cell line expressing a specific surface antigen recognized by selected cells.

14. The method of claim 11 wherein the specific surface antigen is HBsAg and the selected cells are hepatic cells.

15. The method of claim 11 wherein the specific surface antigens are HIV envelope glycoproteins and the selected cells express CD4 antigen on their surface.

16. The method of claim 11 further comprising collecting the packaged delta viral RNA complex budded from the membrane of the infected cells.

17. The method of claim 6 wherein a greater than unit length delta sequence is cloned into a prokaryotic expression vector downstream from a bacteriophage RNA polymerase promoter.

18. The method of claim 17 wherein the vector is derived from a bacterial plasmid and the promoter is derived from bacteriophage selected from the group consisting of T7 and SP6.

19. The method of claim 18 wherein the vector is selected from the group consisting of PBR322 and PUC.

20. The method of claim 1 further comprising providing at least one additional ribozyme to those needed for normal delta replication, positioned at a point in the genome which does not interrupt any critical RNA structures, which will cleave in trans only when the targeted sequence is bound.

* * * * *